United States Patent [19]

Gallagher et al.

[11] Patent Number: 5,773,448

[45] Date of Patent: Jun. 30, 1998

[54] PHARMACEUTICAL COMPOUNDS

[75] Inventors: Peter Thaddeus Gallagher, Yateley; William Martin Owton, Lightwater; Colin William Smith, Bracknell, all of United Kingdom

[73] Assignee: Eli Lilly and Company Limited, Basingstoke, England

[21] Appl. No.: 833,239

[22] Filed: Apr. 14, 1997

Related U.S. Application Data

[63] Continuation of Ser. No. 771,339, Dec. 16, 1996, abandoned.

[30] Foreign Application Priority Data

Dec. 19, 1995 [GB] United Kingdom ............... 9525963

[51] Int. Cl.⁶ ...................... A61K 31/445; C07D 401/06
[52] U.S. Cl. ..................... 514/323; 514/409; 514/414; 546/201; 548/411; 548/465
[58] Field of Search ................ 514/323, 255, 514/409, 414; 546/201; 544/373; 548/411, 465

[56] References Cited

U.S. PATENT DOCUMENTS

| | | | |
|---|---|---|---|
| 4,035,369 | 7/1977 | Vandenberk et al. | 260/293.6 |
| 4,254,127 | 3/1981 | Vandenberk et al. | 424/263 |
| 4,411,890 | 10/1983 | Momany | 548/495 |
| 4,432,978 | 2/1984 | Welch et al. | 424/249 |
| 4,522,824 | 6/1985 | Wagnon et al. | 424/177 |
| 4,547,507 | 10/1985 | Rowlands et al. | 514/291 |
| 4,658,038 | 4/1987 | Tamir et al. | 548/495 |
| 4,680,296 | 7/1987 | Manoury et al. | 514/259 |
| 4,789,676 | 12/1988 | Hibert et al. | 424/249 |
| 4,968,705 | 11/1990 | Reginer et al. | 514/323 |
| 5,081,128 | 1/1992 | George et al. | 514/323 |
| 5,096,900 | 3/1992 | George et al. | 514/213 |
| 5,324,737 | 6/1994 | D'Ambra et al. | 514/323 |
| 5,328,920 | 7/1994 | Effland et al. | 514/339 |
| 5,434,148 | 7/1995 | Yamada et al. | 514/213 |
| 5,563,147 | 10/1996 | Gilmore et al. | 514/292 |

FOREIGN PATENT DOCUMENTS

| | | |
|---|---|---|
| 099303 | 1/1984 | European Pat. Off. . |
| 0 144 230 | 6/1985 | European Pat. Off. . |
| 144729 | 6/1985 | European Pat. Off. . |
| 445862 | 9/1991 | European Pat. Off. . |
| 454330 | 10/1991 | European Pat. Off. . |
| 560235 | 9/1993 | European Pat. Off. . |
| 562832 | 9/1993 | European Pat. Off. . |
| WO 91/16323 | 10/1991 | WIPO . |
| WO 93/12085 | 6/1993 | WIPO . |
| WO 94/11012 | 5/1994 | WIPO . |
| WO 94/13696 | 6/1994 | WIPO . |
| WO 94/19367 | 9/1994 | WIPO . |
| WO 95/17422 | 6/1995 | WIPO . |
| WO 95/17423 | 6/1995 | WIPO . |
| WO 96/15148 | 5/1996 | WIPO . |

OTHER PUBLICATIONS

Smith, et al., *Science*, "A Nonpeptidyl Growth Hormone Secretagogue", vol. 260, pp. 1640–1643, Jun. 11, 1993.

Slide of Presentation on "Genentech Growth Hormone Secretagogues" by Todd Somers, at Serano Symposium on Growth Hormone Secretagogues, in St. Petersburg, Florida, Dec. 5–8, 1994.

McDowell, et al., Proc. Natl. Acad. Sci. USA, 92, 11165–11169 (Nov. 1995) "Growth hormone secretagogues: Characterization, efficacy, and minimal bioactive conformation".

Jerome R. Bagley, et al., *J. Med. Chem.*, 1991, 34, 827–841.

Bigg, D., et al., *New 1-((1-arylpyrrolidin-2-yl)methyl)piperazine derivs.*, Derwent WPI abstract (FR 2684374), 1993.

Sasaki, et al., *Benzoylpiperidine derivatives and their salts as serotonin receptor antagonists*, Chemical Abstracts, vol. 114, 1991, p. 143160 (JP02,264,773).

Gueremy, et al., *Naphthosultam derivatives as serotonin antagonists*, Derwent WPI abstract (WO91/16323), 1990.

*Primary Examiner*—Joseph McKane
*Attorney, Agent, or Firm*—Robert D. Titus; David E. Boone

[57] ABSTRACT

A pharmaceutical compound of the formula

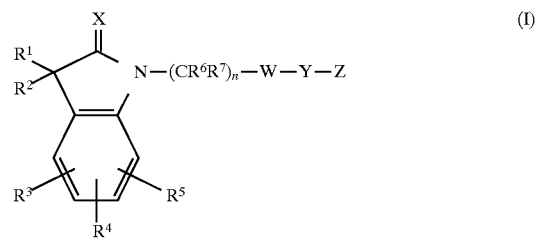

and salts and esters thereof.

6 Claims, No Drawings

PHARMACEUTICAL COMPOUNDS

This application is a continuation of application Ser. No. 08/771,339, filed on Dec. 16, 1996, now abandoned.

FIELD OF INVENTION

This application claims the benefit of United Kingdom Application No. 9525963.6, filed Dec. 19, 1995.

This invention relates to pharmaceutical compounds, their preparation and use.

Compounds of the indole-2-one type have been described in the literature as having potential use as analgesics or for treating cognitive disorders or as cholinesterase inhibitors as, for example, in *J. Med. Chem.* 1991, 34, 827–841, WO 93/12085 and CA 119: 225964t.

SUMMARY OF THE INVENTION

The compounds of the invention are of the formula:

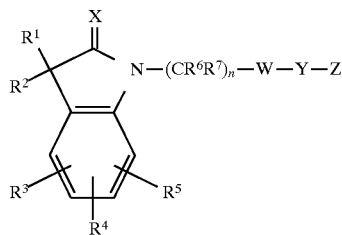

(I)

in which
R¹ and R² are each hydrogen, $C_{1-4}$ alkyl, $C_{1-4}$ alkoxy, HO-$C_{1-4}$ alkyl, $C_{1-4}$ alkoxy-$C_{1-4}$ alkyl, $C_{1-4}$ alkylthio, halo, Ph, PhCR'R"—where Ph is optionally substituted phenyl and R' and R" are each hydrogen or $C_{1-4}$ alkyl, or R¹ and R² together with the carbon atom to which they are attached form a $C_{3-6}$ cycloalkyl group, >C=O, >C=NOR' where R' is hydrogen or $C_{1-4}$ alkyl,
R³, R⁴ and R⁵ are each hydrogen, halo, nitro, $C_{1-4}$ alkyl, $C_{1-4}$ alkoxy, $C_{1-4}$ alkylthio, $C_{1-4}$ alkyl-CO—, $C_{1-4}$ alkyl-S(O)$_m$— where m is 0, 1 or 2, R'R"N—SO$_2$—, —COOR', —CONR'R", —NR'R", —N(OR')COOR", —COR', —NHSO$_2$R', where R' and R" are each hydrogen or $C_{1-4}$ alkyl,
R⁶ and R⁷ are each hydrogen or $C_{1-4}$ alkyl, and n is 1 to 6,
X is oxygen or sulphur,
W is

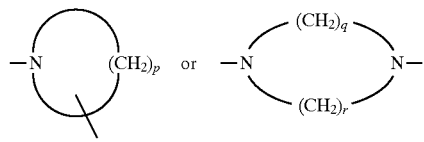

where p is 4 to 7, and q and r are each 1 to 3,
Y is >CO or —CH(OH)—,
and
Z is optionally substituted phenyl or optionally substituted heteroaryl;
and salts and esters thereof.

The compounds of the invention are indicated for use in the treatment of disorders of the central nervous system. They are active in tests that indicate serotonergic modulation.

DETAILED DESCRIPTION OF THE INVENTION

In the above formula (I), a $C_{1-4}$ alkyl group includes methyl, ethyl, propyl, isopropyl, butyl and tert. butyl, and is preferably methyl or ethyl. A $C_{1-4}$ alkoxy group is one such alkyl group linked to a ring via an oxygen atom, and a halo atom is preferably chlorine, bromine or fluorine, and especially chlorine or fluorine. A substituted phenyl group is phenyl substituted with one or more, for example one to three, substituents selected from, for example $C_{1-4}$ alkyl, especially methyl, $C_{1-4}$ alkoxy, especially methoxy and ethoxy, hydroxy, nitro, cyano, halo, especially chloro or fluoro, trihalomethyl, especially trifluoromethyl, carboxy and $C_{1-4}$ alkoxy-carbonyl.

A heteroaryl group can have one or more hetero atoms selected from, for example, oxygen, nitrogen and sulphur and preferably contains from 5 to 10 carbon atoms. Preferably a heteroaryl group contains a single hetero atom and is of the formula:

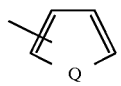

where Q is —O—, —S— or —NR—, and R is hydrogen or $C_{1-6}$ alkyl. Alternatively, a heteroaryl group can comprise a benzene fused ring as, for example:

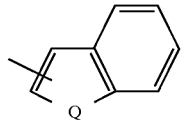

Further heteroaryl groups include those of the formula:

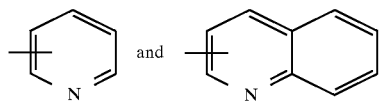

When n is greater than 1, the values of R⁶ and R⁷ need not be identical in each repeating methylene unit.

Preferred compounds are those having one or more of the following features:
(i) X is oxygen
(ii) R¹ and R² are each hydrogen, $C_{1-4}$ alkyl, $C_{1-4}$ alkylthio or benzyl
(iii) R¹ and R² are both methyl
(iv) R¹ is hydrogen and R² is methyl
(v) R³, R⁴ and R⁵ are each hydrogen, halo or $C_{1-4}$ alkyl
(vi) R⁶ and R⁷ are both hydrogen
(vii) n is 2
(viii) W is

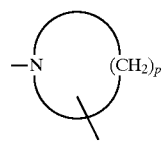

(ix) p is 5
(x) Y is >CO
(xi) Z is optionally substituted phenyl

A preferred group of compounds is of the formula:

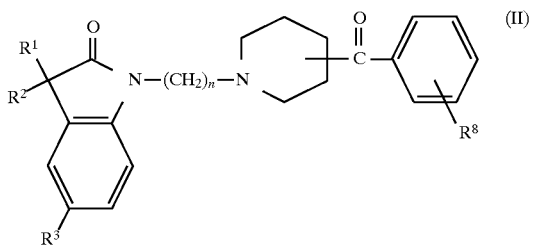

and preferably one in which $R^1$ and $R^2$ are each hydrogen or $C_{1-4}$ alkyl, $R^3$ is hydrogen, $C_{1-4}$ alkyl or halo, n is 2, and $R^8$ is hydrogen or halo. Preferably the benzoyl substituent is attached to the piperidinyl ring at the 4-position. A particularly preferred group is one in which $R^1$ and $R^2$ are both hydrogen and $R^3$ is hydrogen or fluoro, n is 2 and R8 is halo, preferably fluoro; and salts thereof.

It will be appreciated that the compounds of the invention can contain one or more asymmetric carbon atoms which gives rise to isomers. The compounds are normally prepared as racemic mixtures and can conveniently be used as such, but individual isomers can be isolated by conventional techniques if so desired. Such racemic mixtures and individual optical isomers form part of the present invention. It is preferred to use an enantiomerically pure form.

It is, of course, possible to prepare salts and esters of the compounds of the invention and such salts and esters are included in the invention. Salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, Q-acetoxybenzoic, or organic sulphonic, 2-hydroxyethane sulphonic, toluene-p-sulphonic, or naphthalene-2-sulphonic acid.

In addition to pharmaceutically-acceptable salts, other salts are included in the invention. They may serve as intermediates in the purification of compounds or in the preparation of other, for example pharmaceutically-acceptable, acid addition salts, or are useful for identification, characterisation or purification.

The compounds can also be utilised in ester form, such esters being aliphatic or aromatic. The most preferred esters are alkyl esters derived from $C_{1-4}$ alkanols, especially methyl and ethyl esters.

The invention also includes a process for producing a compound of formula (I) above, which comprises reacting a compound of the formula H-W-Y-Z (III) with a compound of the formula:

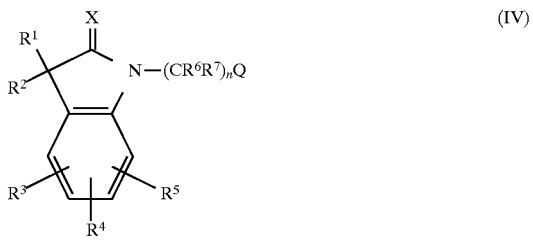

where the substituents have the values given above, and Q is a leaving group, for example, halo or a mesylate or tosylate.

The reaction is preferably carried out in an inert organic solvent such as, for example, methyl isobutyl ketone or acetonitrile, and at a temperature of from 80° C. to 110° C. The reaction takes place in alkaline conditions by the use of, for example, sodium carbonate or potassium carbonate.

Compounds of formula (III) are either known or can be prepared by methods well known in the art.

In the case of compounds in which W is

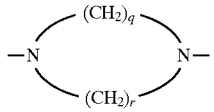

compounds can be prepared reacting the partially protected nitrogen containing cyclic amine with a phenyl or heteroaryl carbonyl halide, followed by deprotection, to give compounds of the formula:

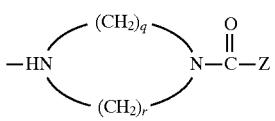

optionally followed by reduction to give the compound of formula (III) in which Y is —CH(OH)—.

Compounds of formula (IV) are either known or can be prepared by methods well known in the art as, for example, by reacting a compound of the formula:

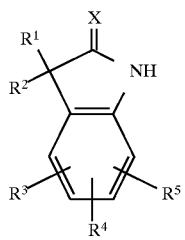

with a compound of the formula $Q'(CR^6R^7)_nQ$, where Q' is also a leaving group.

An alternative route to the compounds of the invention consists of an analogous, reverse, condensation of the principal components of the molecule as, for example, by reacting a compound of the formula (V) above, with a compound of the formula $Q(CR^6R^7)_n$-W-Y-Z Such reagents can be made as described above or by analogous methods.

As mentioned above, the compounds of the invention have useful central nervous system activity. The compounds are active at the serotonin, $5\text{-HT}_{1D\alpha}$, receptor. Their binding activity has been demonstrated in a test described by Zgombick, J. M. et al., Molecular Pharmacology Vol. 40 1992, pages 1036–1042, and compounds of the invention as described in the following Examples have a Ki of from 2 nM to 5,000 nM. Some of the compounds, for example those of formula III, also possess binding activity at the $5\text{-HT}_{1D\beta}$ receptor. Furthermore, compounds have activity at the 5-HT2A receptors as shown in the test described by Leysen, J. E. et al., Molecular Pharmacology Vol. 21 1981, pages 301–314.

Because of their selective affinity for the 5-HT receptors, the compounds of the present invention are indicated for use in treating a variety of conditions such as obesity, bulimia, alcoholism, pain, depression, hypertension, ageing, memory loss, sexual dysfunction, anxiety, schizophrenia, gastrointestinal disorders, headache, cardiovascular disorders, smoking cessation, drug addiction, emesis, Alzheimer's and sleep disorders.

The compounds of the invention are effective over a wide dosage range, the actual dose administered being dependent on such factors as the particular compound being used, the condition being treated and the type and size of mammal being treated. However, the dosage required will normally fall within the range of 0.01 to 20 mg/kg per day, for example in the treatment of adult humans, dosages of from 0.5 to 100 mg per day may be used.

The compounds of the invention will normally be administered orally or by injection and, for this purpose, the compounds will usually be utilised in the form of a pharmaceutical composition. Such compositions are prepared in a manner well known in the pharmaceutical art and comprise at least one active compound.

Accordingly the invention includes a pharmaceutical composition comprising as active ingredient a compound of formula (I) or a pharmaceutically acceptable salt or solvate thereof, associated with a pharmaceutically acceptable excipient. In making the compositions of the invention, the active ingredient will usually be mixed with a carrier, or diluted by a carrier, or enclosed within a carrier which may be in the form of a capsule, sachet, paper or other container. The excipient may be a solid, semi-solid or liquid material which acts as a vehicle, excipient or medium for the active ingredient. Some examples of suitable excipients are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate or oil. The compositions of the invention may, if desired, be formulated so as to provide quick, sustained or delayed release of the active ingredient after administration to the patient.

Depending on the route of administration, the foregoing compositions may be formulated as tablets, capsules or suspensions for oral use and injection solutions or suspensions for parenteral use or as suppositories. Preferably the compositions are formulated in a dosage unit form, each dosage containing from 0.5 to 100 mg, more usually 1 to 100 mg, of the active ingredient.

The following Examples illustrate the invention:

EXAMPLE 1

3,3-Dimethyl-1-(2-hydroxyethyl)-1,3-dihydro-2H-indol-2-one: 3,3-Dimethylindol-1,3-dihydro-2H-indol-2-one (6.3 g, 40 mmol) was dissolved in dry dimethylformamide under nitrogen at room temperature. Sodium hydride (60% dispersion in mineral oil, 1.8 g, 45 mmol) was added and the mixture was stirred until gas evolution ceased. 2-(2-Chloroethoxy)tetrahydro-2H-pyran (7.5 g, 42 mmol) and sodium iodide (0.6 g, 4 mmol) was added and the mixture was warmed to 75° C. for 15 hours. Water was added and the mixture was concentrated under reduced pressure. The residue was taken up in ethyl acetate, washed (×3) with water, dried (MgSO$_4$), filtered and concentrated under reduced pressure. The resulting oil was taken up in methanol, para toluenesulphonic acid (0.75 g, 4 mmol) was added and the mixture was stirred at room temperature for 12 hours. The mixture was concentrated under reduced pressure, taken up in ethyl acetate, washed (×3) with aqueous sodium hydrogen carbonate solution dried (MgSO$_4$), filtered and concentrated under reduced pressure. The resulting oil was purified by chromatography on silica gel, eluent hexane/ethyl acetate, to give 3,3-dimethyl-1-(2-hydroxy-1-ethyl)indol-2(3H)-one which was characterised by $^1$H nmr and MS.

$^1$H NMR (CDCl$_3$) d 1.4(6H s), 3.05 (1H broad), 3.95(4H s), 6.96(1H d), 7.04(1H t), 7.12(2H m).

MS shows 206 (MH$^+$) base peak.

3,3-Dimethyl-1-{2-[4-(4-fluorobenzoyl)-1-piperidinyl]-1-ethyl}-1,3-dihydro-2H-indol-2-one monohydrochloride:

3,3-Dimethyl-1-(2-hydroxyethyl)-1,3-dihydro-2H-indol-2-one (2.05 g, 10 mmol) and triethylamine (1.1 g, 10.9 mmol) was dissolved in dichloromethane under nitrogen and cooled to less than 5° C. in an ice/water bath. Methanesulfonyl chloride (1.3 g, 11.3 mmol) was added and the mixture was stirred for one hour with cooling. The mixture was washed with cold dilute hydrochloric acid, dried (MgSO$_4$), filtered and concentrated under reduced pressure. The resulting oil was dissolved in dry acetonitrile, 4-fluorobenzoylpiperidine para toluenesulfonate (Acros, 2.83 g, 11.7 mmol) potassium carbonate (3 g, 21.7 mmol) and potassium iodide (0.15 g, 0.9 mmol) were added. The mixture was stirred vigorously and heated under gentle reflux for two days. The mixture was poured into chloroform, washed with water, dried (MgSO$_4$), filtered and concentrated under reduced pressure. The resulting oil was taken up in 5N hydrochloric acid whereupon a white solid separated. This solid was recrystallised from ethanol to give 3,3-dimethyl-1-{2-[4-(4-fluorobenzoyl)-1-piperidinyl]-1-ethyl}-1,3-dihydro-2H-indol-2-one monohydrochloride. Melting point 236°–8° C.

EXAMPLE 2

3-Methyl-3-methylthio-1,3-dihydro-2H-indol-2-one:

1,3-Dihydro-2H-indol-2-one (3.3 g,25 mmol) and tetramethylethylenediamine (6.4 g, 55 mmol) was dissolved in freshly distilled tetrahydrofuran under nitrogen and cooled to −75° C. in an acetone/dry ice bath. n-Butyllithium (2.5M, 22 ml, 55 mmol) was added and the mixture was stirred at −75° C. for 30 minutes. Iodomethane (3.57 g, 25 mmol) was added and the mixture was allowed to warm to −20° C., the mixture was recooled to −75° C. then dimethyl disulfide (2.35 g, 25 mmol) was added and the mixture was allowed to warm to room temperature. Water (5 ml) was added and the mixture was concentrated under reduced pressure to a yellow oil. Column chromatography on silica gel (eluent ethyl acetate/hexane) gave 3-methyl-3-methylthio-1,3-dihydro-2H-indol-2-one as a yellow oil which solidified on standing.

$^1$H NMR (CDCl$_3$) d 1.61(3H s), 1.91(3H s), 6.96(1H d), 7.04(1H t), 7.12(2H m), 8.05 (1h broad).

1-(2-Hydroxyethyl)-3-methyl-3-methylthio-1,3-dihydro-2H-indol-2-one:

Prepared from 3-methyl-3-methylthio-1,3-dihydro-2H-indol-2-one and 2-(2-chloroethoxy)tetrahydro-2H-pyran as described in Example 1.

MS shows 238 (MH$^+$) base peak.

1-{2- [4-(4-Fluorobenzoyl)-1-peridinyl]-1-ethyl}-3-methyl-3-methylthio-1,3-dihydro-2H-indol-2-one monohydrochloride:

Prepared from 1-(2-hydroxy-1-ethyl)-3-methyl-3-methylthio-1,3-dihydro-2H-indol-2-one, via the methanesulfonate, and 4-fluorobenzoylpiperidine tosylate as described in Example 1.

Melting point 198°–201° C.

EXAMPLE 3

1-{2- [4-(4-Fluorobenzoyl)-1-piperidinyl]-1-ethyl}-3-methyl-1,3-dihydro-2H-indol-2-one monohydrochloride:

1-{2-[4-(4-Fluorobenzoyl)-1-piperidinyl]-1-ethyl}-3-methyl-3-methylthio-1,3-dihydro-2H-indol-2-one (1.42 g, 3.3 mmol) was dissolved in ethanol, Raney nickel was added and the mixture was stirred at room temperature until TLC indicated reaction was complete. The mixture was filtered and concentrated under reduced pressure to give the crude product which was purified by column chromatography on silica gel (eluent ethyl acetate/hexane). The resulting clear oil was dissolved in ethanol, ethanolic HCl was added and the mixture was concentrated under reduced pressure to give a white solid which recrystallised from 2-propanol to give 1-2-[4-(4-Fluorobenzoyl)-1-piperidinyl]-1-ethyl}-3-methyl-1,3 -dihydro-2H-indol-2-one monohydrochloride. Melting point 209°–211° C.

EXAMPLE 4

3-Benzyl-3-methylthio-1,3-dihydro-2H-indol-2-one:

3-Phenylmethyl-1,3-dihydro-2H-indol-2-one (4 g, 18.25 mmol) (prepared from 1,3-dihydro-2H-indol-2-one and benzaldehyde by the method of Daisley and Walker J. Chem. Soc. (C) (1971) page 1373) and tetramethylethylenediamine (4.5 g, 38.7 mmol) was dissolved in freshly distilled tetrahydrofuran under nitrogen and cooled to −75° C. in an acetone/dry ice bath. n-Butyllithium (2.5M, 20 ml, 50 mmol) was added and the mixture was stirred at −75° C. for 30 minutes. Dimethyl disulfide (1.65 g, 17.6 mmol) was added and the mixture was allowed to warm to room temperature. Water (5 ml) was added and the mixture was concentrated under reduced pressure to a yellow oil. Column chromatography on silica gel (eluent ethyl acetate/hexane) gave 3-methylthio-3-phenylmethyl-1,3-dihydro-2H-indol-2-one as a yellow oil which solidified on standing.

$^1$H NMR (CDCl$_3$) d 1.91(3H s), 3.25(1H d), 3.42(1H d), 6.76(1H d), 6.94(1H t), 7.12(5H m), 7.20(1H t), 7.28(lH t), 8.08(1H broad).

1-(2-Hydroxyethyl)-3-methylthio-3-phenylmethyl-1,3-dihydro-2H-indol-2-one:

Prepared from 3-methylthio-3-phenylmethyl-1,3-dihydro-2H-indol-2-one and 2-(2-chloroethoxy)tetrahydro-2H-pyran as described in Example 1.

MS shows 314 (MH$^+$) base peak.

1-{2-[4-(4-Fluorobenzoyl)-1-piperidinyl]-1-ethyl}-3-methylthio-3-phenylmethyl-1,3-dihydro-2H-indol-2-one monohydrochloride:

Prepared from 1-(2-hydroxyethyl)-3-methylthio-3-phenylmethyl-1,3-dihydro-2H-indol-2-one, via the methanesulfonate, and 4-fluorobenzoylpiperidine tosylate as described in Example 1.

Melting point 182°–184° C.

EXAMPLE 5

1-{2-[4-(4-Fluorobenzoyl)-1-piperidinyl]-1-ethyl}-3-phenylmethyl-1,3-dihydro-2H-indol-2-one monohydrochloride:

Prepared by Raney Nickel reduction of 1-{2-[4-(4-fluorobenzoyl)-1-piperidinyl]-1-ethyl}-3-methylthio-3-phenylmethyl-1,3-dihydro-2H-indol-2-one as described in Example 1.

Melting point 213°–216° C.

EXAMPLE 6

3-Methyl-3-phenylmethyl-1,3-dihydro-2H-indol-2-one:

3-Phenylmethyl-1,3-dihydro-2H-indol-2-one (prepared from 1,3-dihydro-2H-indol-2-one (4 g, 18.25 mmol) and benzaldehyde by the method of Daisley and Walker J. Chem. Soc. (C) (1971) page 1373) and tetramethylethylenediamine (4.5 g, 38.7 mmol) was dissolved in freshly distilled tetrahydrofuran under nitrogen and cooled to −75° C. in an acetone/dry ice bath. n-Butyllithium (2.5M, 20 ml, 50 mmol) was added and the mixture was stirred at −75° C. for 30 minutes. Iodomethane (2.84 g, 20 mmol) was added and the mixture was allowed to warm to room temperature. Water (5 ml) was added and the mixture was concentrated under reduced pressure to a yellow oil. Column chromatography on silica gel (eluent ethyl acetate/hexane) gave 3-methyl-3-phenylmethyl-1,3-dihydro-2H-indol-2-one as a yellow oil which solidified on standing.

MS shows 238 (MH$^+$) base peak and 255 (M+NH$_4^+$).

3-Benzyl-1-(2-hydrox-1-ethyl)-3-methylindol-2(3H)-one:

Prepared from 3-benzyl-3-methylindol-2(3H)-one and 2-(2-chloroethoxy)tetrahydro-2H-pyran.

MS shows 282 (MH$^+$) base peak.

1-{2-[4-(4-Fluorobenzoyl)-1-piperidinyl]-1-ethyl}-3-methyl-3-phenylmethyl-1,3-dihydro-2H-indol-2-one monohydrochloride:

Prepared from 1-(2-hydroxyethyl)-3-methyl-3-phenylmethyl-1,3-dihydro-2H-indol-2-one, via the methanesulfonate, and 4-fluorobenzoylpiperidine tosylate.

Melting point 204°–207° C.

EXAMPLE 7

3-Ethyl-1-(2-hydroxyethyl)-3-methyl-1,3-dihydro-2H-indol-2-one:

Prepared from 3-ethyl-3-methyl-1,3-dihydro-2H-indol-2-one (prepared by the method of Endler and Becker; Organic Syntheses Coll. vol. 4 page 657) and 2-(2-chloroethoxy)tetrahydro-2H-pyran.

MS shows 220 (MH$^+$) base peak.

3-Ethyl-1-{2-[4-(4-Fluorobenzoyl)-1-piperidinyl]-1-ethyl}-3-methyl-1,3-dihydro-2H-indol-2-one monohydrochloride:

Prepared from 3-ethyl-1-(2-hydroxyethyl)-3-methyl-1,3-dihydro-2H-indol-2-one, via the methanesulfonate, and 4-fluorobenzoylpiperidine tosylate as described above.

Melting point 210°–212° C.

EXAMPLE 8

3-(1-Methylethyl)-3-methylthio-1,3-dihydro-2H-indol-2-one:

Prepared from 3-(1-methylethyl)-1,3-dihydro-2H-indol-2-one (prepared from 1,3-dihydro-2H-indol-2-one and acetone by the method of Daisley and Walker, J. Chem. Soc. (C) (1971) page 1373) by the method described above for 3-methylthio-3-phenylmethyl-1,3-dihydro-2H-indol-2-one.

MS shows 222 (M$^+$) base peak.

1-(2-Hydroxyethyl)-3-(1-methylethyl)-3-methylthio-1,3-dihydro-2H-indol-2-one:

Prepared from 3-(1-methylethyl)-3-methylthio-1,3-dihydro-2H-indol-2-one and 2-(2-chloroethoxy)tetrahydro-2H-pyran.

MS shows 266 (MH$^+$) base peak.

1-{2-[4-(4-Fluorobenzoyl)-1-piperidinyl]-1-ethyl}-3-(1-methylethyl)-3-methylthio-1,3-dihydro-2H-indol-2-one monohydrochloride:

Prepared from 1-(2-hydroxyethyl)-3-(1-methylethyl)-3-methylthio-1,3-dihydro-2H-indol-2-one, via the methanesulfonate, and 4-fluorobenzoylpiperidine tosylate.

Melting point 150°–152° C.

EXAMPLE 9

1-{2-[4-(4-Fluorobenzoyl)-1-piperidinyll-1-ethyl}-3-(1-methylethyl)-1,3-dihydro-2H-indol-2-one monohydrochloride Prepared by Raney Nickel reduction of 1-{2-[4-(4-fluorobenzoyl)-1-piperidinyl]-1-ethyl}-3-(1-methylethyl)-3-methylthio-1,3-dihydro-2H-indol-2-one as described above.

Melting point 207°–209° C.

EXAMPLE 10

5-Bromo-3,3-dimethyl-1,3-dihydro-2H-indol-2-one:

3,3-Dimethyl-1,3-dihydro-2H-indol-2-one (1.12 g, 6.95 mmol) was dissolved in chloroform and stirred at room temperature under nitrogen. Bromine (1.12 g) was added and the mixture was heated under reflux until HBr evolution ceased and the bromine colour was discharged from the solution. The solution was washed with sodium metabisulphite solution and sodium hydrogen carbonate solution, dried ($MgSO_4$), filtered and concentrated to dry under reduced pressure to give 5-bromo-3,3-dimethyl-1,3-dihydro-2H-indol-2-one as a yellow solid.

$^1$H NMR ($CDCl_3$) d1.39 (6H s), 6.8 (1H d), 7.3 (2H m), 7.9 (1H broad)

5-Bromo-3,3-dimethyl-1-(2-hydroxyethyl)-1 3-dihydro-2H-indol-2-one:

Prepared from 5-bromo-3,3-dimethyl-1,3-dihydro-2H-indol-2-one and 2-(2-chloroethoxy)tetrahydro-2H-pyran.

$^1$H NMR ($CDCl_3$) d1.39 (6H s), 3.05 (1H broad), 3.95(4H s), 6.8 (1H d), 7.3 (2H m), 5-Bromo-3,3-dimethyl-1-{2-{4-(4-Fluorobenzoyl)-1-piperidinyl]-1-ethyl}-1,3-dihydro-2H-indol-2-one monohydrochloride:

Prepared from 5-bromo-3,3-dimethyl-1-(2-hydroxyethyl)-1,3-dihydro-2H-indol-2-one, via the methanesulfonate, and 4-fluorobenzoylpiperidine tosylate.

Melting point 208°–211° C.

EXAMPLE 11

3,3-Dimethyl-5-methanesulfonyl-1,3-dihydro-2H-indol-2-one:

5-Bromo-3,3-dimethyl-1,3-dihydro-2H-indol-2-one (2 g, 8.3 mmol) was dissolved in freshly distilled tetrahydrofuran with tetramethylethylenediamine (2 g, 17.2 mmol) and was cooled to −75° C. under nitrogen. n-Butyllithium in hexane (2.5M, 8 ml, 20 mmol) was added and the mixture was stirred at −75° C. for 40 minutes. Dimethyl disulfide (1 g, 10.6 mmol) was added and the mixture was allowed to warm to room temperature. Water (5 ml) was added and the mixture was concentrated under reduced pressure, the resulting oil was taken up in dichloromethane, washed with dilute hydrochloric acid, dried ($MgSO_4$), filtered and concentrated to dry under reduced pressure. The resulting oil was taken up in acetic acid, sodium perborate (7 g, 45 mmol) was added and the mixture was stirred at 50° C. overnight. The mixture was poured into water and extracted with ethyl acetate. The combined organic phases were washed with 2N sodium hydroxide solution, dried ($MgSO_4$), filtered and concentrated under reduced pressure. Column chromatography on silica gel (eluent ethyl acetate/hexane) gave 3,3-dimethyl-5-methanesulfonyl-1,3-dihydro-2H-indol-2-one as a pale yellow solid.

MS shows 240 (MH$^+$) base peak and 257 (M+NH$_4$).

3,3-Dimethyl-1-(2-hydroxyethyl)-5-methanesulfonyl-1,3-dihydro-2H-indol-2-one:

Prepared from 3,3-dimethyl-5-methanesulfonyl-1,3-dihydro-2H-indol-2-one and 2-(2-chloroethoxy)tetrahydro-2H-pyran.

$^1$H NMR ($CDCl_3$) d1.41 (6H s), 2.5 (lH broad), 3.05 (3H s), 3.95(4H s), 7.18 (1H d), 7.76 (1H s), 7.84 (1H d)

3,3-Dimethyl-1-{2-{4-(4-fluorobenzoyl)-1-piperidinyl]-1-ethyl}-5-methanesulfonyl-1,3-dihydro-2H-indol-2-one monohydrochloride :

Prepared from 3,3-dimethyl-1-(2-hydroxyethyl)-5-methanesulfonyl-1,3-dihydro-2H-indol-2-one, via the methanesulfonate, and 4-fluorobenzoyl piperidine tosylate.

Melting point 223°–226° C.

EXAMPLE 12

3,3-Dimethyl-5-fluoro-1-(2-hydroxyethyl)-1,3-dihydro-2H-indol-2-one:

5-Fluoro-1,3-dihydro-2H-indol-2-one (2.4 g, 15.9 mmol) (prepared according to the method of Clark et al., Synthesis (1991) 871) was dissolved in freshly distilled tetrahydrofuran with tetramethylethylenediamine (3.7 g, 31.9 mmol) and was cooled to −75° C. under nitrogen. nButyllithium (2.4 equivalents) was added and the mixture was stirred at −75° C. for 40 minutes. Iodomethane (9 g, 63 mmol) was added and the mixture was allowed to warm to room temperature. After two hours' stirring at this temperature, water (5 ml) was added and the mixture was concentrated under reduced pressure, the resulting oil was taken up in dichloromethane, washed with dilute hydrochloric acid, dried ($MgSO_4$), filtered and concentrated to dry under reduced pressure to give a yellow oil. This oil was dissolved in N-methylpyrrolidone and stirred at room temperature under nitrogen. Sodium hydride (0.625 g, 15.6 mmol) was added and the mixture was stirred until gas evolution ceased. 2-(2-Chloroethoxy)tetrahydro-2H-pyran (2.5 g, 15 mmol) and sodium iodide (0.1 g, 0.66 mmol) was added and the mixture was warmed to 75° C. for 15 hours. Water was added and the mixture was concentrated under reduced pressure. The residue was taken up in ethyl acetate, washed (×3) with water, dried ($MgSO_4$), filtered and concentrated under reduced pressure. The resulting oil was taken up in methanol, para toluenesulphonic acid (0.1 g, 0.5 mmol) was added and the mixture was stirred at room temperature for 12 hours. The mixture was concentrated under reduced pressure, taken up in ethyl acetate, washed (×3) with aqueous sodium hydrogen carbonate solution dried ($MgSO_4$), filtered and concentrated under reduced pressure. The resulting oil was purified by column chromatography on silica gel, (eluent hexane/ethyl acetate) to give 3,3-dimethyl-5-fluoro-1-(2-hydroxyethyl)-1,3-dihydro-2H-indol-2-one as a yellow oil.

MS shows 224 (MH$^+$) base peak and 241 (M+NH$_4$)

3,3-Dimethyl-5-fluoro-1-{2-[4-(4-fluorobenzoyl)-1-piperidinyl]-1-ethyl}-1,3-dihydro-2H-indol-2-one monohydrochloride:

Prepared from 3,3-dimethyl-5-fluoro-1-(2-hydroxyethyl)-1,3-dihydro-2H-indol-2-one, via the methanesulfonate, and 4-fluorobenzoyl piperidine tosylate as described above.

Melting point 221°–223° C.

EXAMPLE 13

5,6-Difluro-3,3-dimethyl-1,3-dihydro-2H-indol-2-one:

3,4-Difluoroacetonitrile (5 g, 32.7 mmol) was added dropwise to 90% fuming nitric acid (25 ml) stirred and cooled in an ice/water bath. After 15 hours' stirring the mixture was poured into water, neutralised with sodium bicarbonate and extracted into dichloromethane. The organic phase was dried (MgSO$_4$), filtered and concentrated under reduced pressure. The resulting oil was dissolved in boron trifluoride acetic acid complex (30 ml), water (1 ml) was added and the mixture was heated under reflux for three hours. The mixture was poured into water, the pH was adjusted to pH4 and the mixture was extracted with ethyl acetate. The organic phase was dried (MgSO$_4$), filtered and concentrated under reduced pressure. The resulting oily solid was dissolved in acetic acid, iron powder was added and the mixture was heated under reflux for 1 hour. The mixture was filtered through Celite and concentrated under reduced pressure to a dark oil.

Column chromatography on silica gel (eluent chloroform/methanol) gave 5,6-difluro-3,3-dimethyl-1,3-dihydro-2H-indol-2-one as an orange solid.

$^1$H NMR (CDCl$_3$) d 3.48(2H s), 6.7(1H dd), 7.05(1H dd), 8.65(1H broad)

5.6-Difluro-3,3-dimethyl-1-(2-hydroxyethyl)-1,3-dihydro-2H-indol-2-one:

Prepared 5,6-difluro-3,3-dimethyl-1,3-dihydro-2H-indol-2-one.

$^1$H NMR (CDCl$_3$) d 1.38(6H s), 3.20(1H broad), 3.84(4H m), 6.7(1H dd), 7.03(1H dd)

5,6-Difluro-3,3-dimethyl-1-{2-[4-(4-fluorobenzoyl)-1-pieridinyl]-1-ethyl}-1,3-dihydro-2H-indol-2-one monohydrochloride:

Prepared from 5,6-difluro-3,3-dimethyl-1-(2-hydroxyethyl)-1,3-dihydro-2H-indol-2-one, via the methanesulfonate, and 4-fluorobenzoyl piperidine tosylate as described above.

Melting point 223°–225° C.

EXAMPLE 14

3,3-Dimethyl-1-(2-hydroxyethyl)-4-methoxy-1,3-dihydro-2H-indol-2-one:

Prepared from 3,3-dimethyl-4-methoxy-1,3-dihydro-2H-indol-2-one (prepared according to the method of Clark et al., Synthesis (1991) 871).

$^1$H NMR (CDCl$_3$) d 1.42(6H s), 2.8(1H broad), 3.75(4H m), 3.8(3H s), 6.57(2H t), 7.06(1H dd), 3,3-Dimethyl-1-{2-[4-(4-fluorobenzoyl)-1-piperidinyl]-1-ethyl}-4-methoxy-1,3-dihydro-2H-indol-2-one monohydrochloride:

Prepared from 3,3-dimethyl-1-(2-hydroxyethyl)-4-methoxy-1,3-dihydro-2H-indol-2-one, via the methanesulfonate, and 4-fluorobenzoyl piperidine tosylate.

Melting point 224°–227° C.

EXAMPLE 15

1-(2-Hydroxyethyl)-3,3,5-trimethyl-1,3-dihydro-2H-indol-2-one:

Prepared from 3,3,5-trimethyl-1,3-dihydro-2H-indol-2-one (prepared by the method of Endler and Becker; Organic Syntheses Coll. vol. 4 page 657).

MS shows 220 (MH$^+$) base peak and 237 (M+NH$_4$)

1-{2-[4-(4-Fluorobenzoyl)-1-piperidinyl]-1-ethyl}-3,3,5-trimethyl-1,3-dihydro-2H-indol-2-one monohydrochloride:

Prepared from 1-(2-hydroxyethyl)-3,3,5-trimethyl-1,3-dihydro-2H-indol-2-one, via the methanesulfonate, and 4-fluorobenzoyl piperidine tosylate.

Melting point 228°–230° C.

EXAMPLE 16

5-Chloro-3,3-dimethyl-1-(2-hydroxyethyl)-1,3-dihydro-2H-indol-2-one:

Prepared from 5-chloro-3,3-dimethyl-1,3-dihydro-2H-indol-2-one (prepared by the method of Endler and Becker; Organic Syntheses Coll. vol. 4 page 657).

$^1$H NMR (CDCl$_3$) d1.39 (6H s), 3.05 (1H broad), 3.95(4H s), 6.8 (1H d), 7.3 (2H m), 5-Chloro-3,3-dimethyl-1-{2-[4-(4-fluorobenzoyl)-1-piperidinyl]-1-ethyl}-1,3-dihydro-2H-indol-2-one monohydrochloride:

Prepared from 5-chloro-3,3-dimethyl-1-(2-hydroxyethyl)-1,3-dihydro-2H-indol-2-one, via the methanesulfonate, and 4-fluorobenzoyl piperidine tosylate.

Melting point 175°–176° C.

EXAMPLE 17

1-(2-Hydroxyethyl)-3,3,7-trimethyl-1,3-dihydro-2H-indol-2-one:

Prepared from 3,3,7-trimethyl-1,3-dihydro-2H-indol-2-one (prepared by the method of Endler and Becker; Organic Syntheses Coll. vol. 4 page 657).

MS shows 220 (MH$^+$) base peak and 237 (M+NH$_4$)

1-{2-[4-(4-Fluorobenzoyl)-1-pieridinyl]-1-ethyl}-3,3,7-trimethyl-1,3-dihydro-2H-indol-2-one monohydrochloride.

Prepared from 1-(2-hydroxyethyl)-3,3,7-trimethyl-1,3-dihydro-2H-indol-2-one, via the methanesulfonate, and 4-fluorobenzoyl piperidine tosylate.

Melting point 150°–152° C.

EXAMPLE 18

3,3-Dimethyl-1-(2-hydroxyethyl)-5-methoxy-1,3-dihydro-2H-indol-2-one:

Prepared from 3,3-dimethyl-5-methoxy-1,3-dihydro-2H-indol-2-one (prepared by the method of Endler and Becker; Organic Syntheses Coll. vol. 4 page 657).

$^1$H NMR (CDCl$_3$) δ1.39 (6H s), 3.05 (1H broad), 3.82(3H s), 3.95(4H s), 6.8 (1H d), 7.3 (2H m), 3,3-Dimethyl-1-{2-[4-(4-fluorobenzoyl)-1-piperidinyl]-1-ethyl}-5-methoxy-1,3-dihydro-2H-indol-2-one monohydrochloride:

Prepared from 3,3-dimethyl-1-(2-hydroxyethyl)-5-methoxy-1,3-dihydro-2H-indol-2-one, via the methanesulfonate, and 4-fluorobenzoyl piperidine tosylate.

Melting point 117.5°–118° C.

EXAMPLE 19

3,3,4-Trimethyl-1,3-dihydro-2H-indol-2-one and 3,3,6-trimethyl-1,3-dihydro-2H-indol-2-one:

Prepared from N-isobutyl-3-methylphenylhydrazide by the method of Endler and Becker; Organic Syntheses Coll. vol. 4 page 657 and separated by preparative HPLC.

Melting point—3,3,4-Trimethyl-1,3-dihydro-2H-indol-2-one 133° C.

Melting point—3,3,6-Trimethy-1,3-dihydro-2H-indol-2-one 178° C.

1-(2-Hydroxyethyl)-3,3,4-trimethyl-1,3-dihydro-2H-indol-2-one:

Prepared from 3,3,4-trimethyl-1,3-dihydro-2H-indol-2-one (prepared by the method of Endler and Becker; Organic Syntheses Coll. vol. 4 page 657) as described above.

MS shows 220 (MH$^+$) base peak and 237 (M+NH$_4$)

1-{2-[4-(4-Fluorobenzoyl)-1-piperidinyl]-1-ethyl}-3,3,4-trimethyl-indol-2(3H)-one monohydrochloride:

Prepared from 1-(2-hydroxyethyl)-3,3,4-trimethyl-1,3-dihydro-2H-indol-2-one, via the methanesulfonate, and 4-fluorobenzoyl piperidine tosylate as described above.

Melting point 211°–214° C.

EXAMPLE 20

1-(2-Hydroxyethyl)-3,3,6-trimethyl-1,3-dihydro-2H-indol-2-one:

Prepared from 3,3,6-trimethyl-1,3-dihydro-2H-indol-2-one (prepared by the method of Endler and Becker; Organic Syntheses Coll. vol. 4 page 657) as described above.

MS shows 220 (MH$^+$) base peak and 237 (M+NH$_4$)

1-{2-[4-(4-Fluorobenzoyl)-1-piperidinyl]-1-ethyl}-3,3,6-trimethyl-1,3-dihydro-2H-indol-2-one monohydrochloride:

Prepared from 1-(2-hydroxyethyl)-3,3,6-trimethyl-1,3-dihydro-2H-indol-2-one, via the methanesulfonate, and 4-fluorobenzoyl piperidine tosylate as described above.

Melting point 198.5°–200.5° C.

EXAMPLE 21

1-(2-Chloroethyl)-1,3-dihydro-2H-indol-2-one :

1-(2-Chloroethyl)-lH-indol-2,3-dione (5.24 g) [C.A. Reg no. 77218-99-6] was suspended in acetic acid (50 ml) and hydrogenated at 60 p.s.i., at room temperature, in the presence of 70% perchloric acid (0.2 ml) and 5% palladium on charcoal (1 g) for 24 hours. The clear solution was filtered and concentrated under reduced pressure. The residue was purified by chromatography on silica gel, eluent chloroform, to give 1-(2-chloroethyl)-1,3-dihydro-2H-indol-2-one as a white solid.

Melting point 74° C.

1-{2-[4-(4-Fluorobenzoyl)-1-piperidinyl]-1-ethyl}-1,3-dihydro-2H-indol-2-one hydrochloride:

1-(2-Chloroethyl)-1,3-dihydro-2H-indol-2-one (1.95 g) and 4-fluorobenzoyl piperidine para toluenesulponate (4.1 g) were added to a solution of sodium carbonate (3.18 g) and water (20 ml). The mixture was stirred mechanically at reflux for 9 hours. The hot solution was cooled (ice-water bath) and the hard solid was broken up, filtered, washed with water and dried. The solid was purified by chromatography on silica gel, eluent chloroform-1% methanol, to give an oil. Tne pure freebase was dissolved in a little chloroform, ethanolic HCl was added, the solution was evaporated to dryness and triturated with ether to give 1-{2-[4-(4-fluorobenzoyl)-1-piperidinyl]-1-ethyl}-1,3-dihydro-2H-indol-2-one monohydrochloride as a white solid.

Melting point 206°–213° C.

EXAMPLE 22

1-(2-Chloroethyl)-5-fluoro-1H-indol-2,3-dione:

5-Fluoro-1H-indol-2,3-dione (8.92 g) was dissolved in dimethylformamide (60 ml). Sodium hydride (60% dispersion in mineral oil, 3.08 g) was added in portions with stirring and cooling (ice-water bath) and the mixture was stirred until gas evolution ceased. 1-Bromo-2-chloroethane (5.4 ml, 9.3 g) was added dropwise. The mixture was stirred at room temperature for 24 hours and then quenched into water and extracted into chloroform. The combined organic phases were washed with water, dried (MgSO$_4$), filtered and concentrated under reduced pressure. The resulting oil was purified by chromatography on silica gel, eluent chloroform, to give 1-(2-Chloroethyl)-5-fluoro-1H-indole-2,3-dione as a red solid.

Melting point 103° C.

1-(2-Chloroethyl)-1,3-dihydro-5-fluoro-2-oxo-2H-indole-3-spiro-2'-1,3 dithiane

A solution of 1-(2-chloroethyl)-5-fluoro-1H-indole-2,3-dione (2.27 g), propanedithiol (1.1 ml) in chloroform was added dropwise to a stirred solution of boron trifluoride etherate (1.2 ml) in acetic acid (2.2 ml) and chloroform (10 ml) which was maintained at a gentle reflux throughout the addition. After 1.5 h reaction time the mixture was cooled, washed with water and sodium hydrogen carbonate solution, dried (MgSO$_4$) and filtered through a pad of flash silica using chloroform as eluent. The combined fractions were evaporated under reduced pressure and triturated with ether to give 1-(2-chloroethyl)-1,3-dihydro-5-fluoro-2-oxo-2H-indole-3-spiro-2'-1,3-dithiane.

Melting point 122° C.

EXAMPLE 23

1-(2-Chloroethyl)-5-fluoro-1,3-dihydro-2H-indole-2-one:

1-(2-chloroethyl)-1,3-dihydro-5-fluoro-2-oxo-2H-indole-3-spiro-2'-1,3-dithiane (2.08 g) was dissolved in a mixture of ethanol (30 ml) and tetrahydrofuran (20 ml). Raney nickel was added and the mixture was heated under reflux with vigorous stirring for 3 hours. The cooled solution was filtered, evaporated under reduced pressure and triturated with ether to give 1-(2-Chloroethyl)-5-fluoro-1,3-dihydro-2H-indole-2-one as a white solid.

Melting point 127° C.

1-{2-[4-(4-Fluorobenzoyl)-1-piperidinyl]-1-ethyl}-5-fluoro-1,3-dihydro-2H-indol-2-one hydrochloride:

1-(2-Chloroethyl)-5-fluoro-1,3-dihydro-2H-indole-2-one (0.15 g, 0.737 mmol), 4-fluorobenzoylpiperidine para toluenesulponate (0.307 g, 0.811 mmol) and sodium carbonate (0.258 g, 2.19 mmol) in water (5 ml) were heated under reflux with magnetic stirring for 16 h, cooled ethyl acetae (10 ml) was added and the mixture stirred for 2 h, the ethyl acetate was separated, the aqueous layer extracted with more ethyl acetate (2×20 ml) combined, dried (MgSO$_4$), filtered and the solvent evaporated in vacuo to give a solid which was chromatographed on silica gel eluting with ethyl acetate to give a solid (148 mg). 100 mg of this solid was converted to the hydrochloride with trimethylsilylchloride (0.033 ml) in methanol (8 ml) to give 1-{2-[4-(4-fluorobenzoyl)-1-piperidinyl]-1-ethyl}-5-fluoro-1,3-dihydro-2H-indol-2-one hydrochloride Melting point 221°–223° C.

EXAMPLE 24

1-(2-Chloroethyl)-3,3-difluoro-1,3-dihydro-2H-indole-2-one:

1-(2-Chloroethyl)-1H-indole-2,3-dione (1.1 g, 5.2 mmol) [C.A. Reg no. 77218-99-6] was heated to 65° C. under nitrogen in diethylaminosulfur trifluoride (3 ml). The reaction mixture was poured onto water and extracted with chloroform. The organic phase was washed with sodium hydrogen carbonate solution, dried (MgSO$_4$) and filtered to give 1-(2-chloroethyl)-3,3-difluoro-1,3-dihydro-2H-indole-2-one as a dark oil.

MS shows 231 and 233 (MH$^+$)

1-{2-[4-(4-Fluorobenzoyl)-1-piperidinyl]-1-ethyl}-3,3-difluoro-1,3-dihydro-2H-indole-2-one monohydrochloride:

1-(2-Chloroethyl)-3,3-difluoro-1,3-dihydro-2H-indole-2-one (0.85 g, 3.67 mmol), 4-fluorobenzoyl piperidine para toluenesulphonate salt (1.4 g, 3.68 mmol), potassium carbonate (1.2 g, 8.7 mmol) and potassium iodide (0.1 g, 0.6 mmol)) were dissolved in N-methyl pyrrolidone and heated with stirring to 85° C. for 6 hours. The reaction mixture was poured into water and extracted into ethyl acetate. dried (MgSO$_4$), filtered and concentrated under reduced pressure. The resulting oil was purified by chromatography on silica gel, eluent hexane/ethyl acetate, to give a yellow oil. The oil was dissolved in ethanol, ethanolic HCl was added and the mixture was concentrated under reduced pressure to give a white solid. This was taken up in hot ethyl acetate and refrigerated whereupon a white solid precipitated, this was collected by filtration to give 1-{2-[4-(4-Fluorobenzoyl)-1-piperidinyl]-1-ethyl}-3,3-difluorol-(2-chloroethyl)-3,3-difluoro-1,3-dihydro-2H-indole-2-one mono hydrochloride Melting point 202°–205° C.

EXAMPLE 25

1-(2-Chloroethyl)-3,3,5-triifluoro-1,3-dihydro-2H-indole-2-one:

Prepared from 1-(2-chloroethyl)-5-fluoro-1H-indole-2,3-dione and diethylaminosulfur trifluoride.

MS shows 249 and 251 (MH$^+$)

1-{2-[4-(4-Fluorobenzoyl)-1-piperidinyl]-1-ethyl}-3,3,5-trifluoro-1,3-dihydro-2H-indole-2-one monohydrochloride:

Prepared from 1-(2-chloroethyl)-3,3,5-trifluoro-1,3-dihydro-2H-indole-2-one and 4-fluorobenzoyl piperidine.

Melting point 209°–212° C.

EXAMPLE 26

1-Acetyl-1,3-dihydro-2H-indol-2-one:

1,3-Dihydro-2H-indol-2-one (35.6 g, 0.268mol) suspended in acetic anhydride (30 ml) and mixture refluxed for 20 hours. Filtered and washed with diethyl ether (50 ml) dried in vacuo at 80° C. to give a solid.

3-Spirocyclopropyl-1,3-dihydro-2H-indol-2-one:
1-Acetyl-1,3-dihydro-2H-indol-2-one (15.0 g, 85.7 mmol) dissolved in dimethylformamide (180 ml) and added to suspension of sodium hydride (60% in oil dispersion, 7.2 g, 4.32 g, 0.18 mol) in dimethylformamide (30 ml). After 30 minutes 1,2-dibromoethane (17.71 g, 94.27 mmol) was added and the mixture stirred at ambient temperature for 20 hours. More sodium hydride (1.4 g, 0.84 g, 14 mmol) was added followed by 1,2-dibromoethane (4 g, 21.96 mmol) and stirred for 1h at ambient temperature. The solvent was removed in vacuo and the residue treated with water (100 ml) added extracted with ethyl acetate (2×150 ml), separated and dried (MgSO$_4$), filtered and concentrated in vacuo to give an oil which was purified by column chromatography on silica eluting with ethyl acetate/hexane to give an oil.

$^1$H NMR (CDCl$_3$) δ1.54 (2H m), 1.78 (2H m), 6.82 (1H d), 7.02 (2H m), 7.22 (1H m), 9.0 (1H broad)

EXAMPLE 27

1-(2-Hydroxyethyl)-3-spirocyclopropyl-1,3-dihydro-2H-indol-2-one:

Prepared from 3-spirocyclopropyl-1,3-dihydro-2H-indol-2-one and 2-(2-chloroethoxy)tetrahydro-2H-pyran.

$^1$H NMR (CDCl$_3$) δ1.54 (2H m), 1.78 (2H m), 3.85 (4H m), 6.82 (1H d), 7.02 (2H m), 7.22 (1H m)

1-(2-(4-(4-fluorobenzoyl)-1-piperidinyl)-1-ethyl)-1,3-dihydro-3-spiro-1-cyclopropyl-2H-indole-2-one monohydrochloride:

Prepared from 1-(2-hydroxyethyl)-3-spirocyclopropyl-1,3-dihydro-2H-indol-2-one via the methanesulfonate, and 4-fluorobenzoylpiperidine tosylate.

Melting point 238°–240° C.

EXAMPLE 28

1-(2-Hydroxyethyl)-3-methyl-3-phenyl-1,3-dihydro-2H-indol-2-one: Prepared from 3-methyl-3-phenyl-1,3-dihydro-2H-indol-2-one (prepared by the method of Endler and Becker; Organic Syntheses Coll. vol. 4 page 657) and 2-(2-chloroethoxy)tetrahydro-2H-pyran.

$^1$H NMR (CDCl$_3$) δ1.78 (3H s), 6.82 (1H d), 7.02 (2H m), 7.22 (1H m), 7.3 (5H m), 9.25 (1H broad)

1-(2-(4-(4-Fluorobenzoyl)-1-piperidinyl)-1-ethyl)-3-methyl-3-phenyl-1,3-dihydro-2H-indol-2-one monohydrochloride:

Prepared from 1-(2-hydroxyethyl)-3-methyl-3-phenyl-1,3-dihydro-2H-indol-2-one via the methanesulfonate, and 4-fluorobenzoylpiperidine tosylate.

Melting point 215°–216° C.

EXAMPLE 29

1-(2-(4-(4-Fluorobenzoyl)-1-piperidinyl)-1-ethyl)-1H-indol-2,3-dione monohydrochloride:

Prepared from 1-(2-chloroethyl)-1H-indol-2,3-dione and 4-fluorobenzoyl piperidine para toluenesulfonate and potassium carbonate and sodium iodide in N-methylpyrrolidinone.

Melting point 230°–231° C.

EXAMPLE 30

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 31

Capsules each containing 20 mg of medicament are made as follows:

| Active ingredient | 20 mg |
|---|---|
| Dried starch | 178 mg |
| Magnesium stearate | 2 mg |
| Total | 200 mg |

The active ingredient, starch and magnesium stearate are passed through a sieve and filled into hard gelatine capsules in 200 mg quantities.

What is claimed is:

1. A compound of the formula:

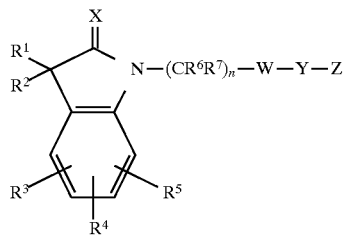

in which $R^1$ and $R^2$ are each hydrogen, $C_{1-4}$ alkyl, $C_{1-4}$ alkoxy, HO-$C_{1-4}$ alkyl, $C_{1-4}$ alkoxy-$C_{1-4}$ alkyl, $C_{1-4}$ alkylthio, halo, Ph, PhCR'R"— where Ph is optionally substituted phenyl and R' and R" are each hydrogen or $C_{1-4}$ alkyl, or $R^1$ and $R^2$ together with the carbon atom to which they are attached form a $C_{3-6}$ cycloalkyl group,

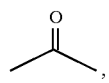

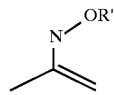

where R' is hydrogen or $C_{1-4}$ alkyl, $R^3$, $R^4$ and $R^5$ are each hydrogen, halo, nitro, $C_{1-4}$ alkyl, $C_{1-4}$ alkoxy, $C_{1-4}$ alkylthio, $C_{1-4}$ alkyl—CO—, $C_{1-4}$ alkyl—S(O)m— where m is 0, 1 or 2, R'R"N—$SO_2$—, —COOR', —CONR'R", —NR'R", —N(OR')COOR", —COR', —$NHSO_2$R', where R' and R" are each hydrogen or $C_{1-4}$ alkyl, R6 and $R^7$ are each hydrogen or $C_{1-4}$ alkyl, and n is 1 to 6, X is oxygen or sulphur, W is

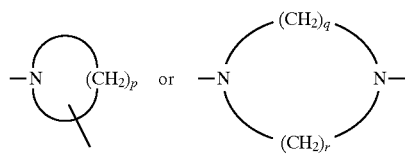

where p is 4 to 7, and q and r are each 1 to 3, y is >CO or —CH(OH)—, and

Z is optionally substituted phenyl or optionally substituted heteroaryl;

and salts and esters thereof.

2. A compound according to claim 1 in which X is oxygen and W is:

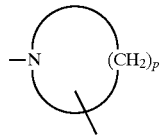

3. A compound according to claim 2 in which Z is optionally substituted phenyl.

4. A compound of the formula:

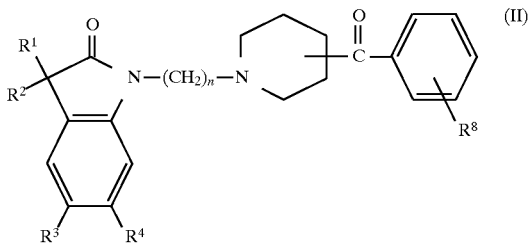

in which $R^1$ and $R^2$ are each hydrogen or $C_{1-4}$ alkyl, $R^3$ and $R^4$ are each hydrogen, $C_{1-4}$ alkyl or halo, n is 2, and $R^8$ is hydrogen or halo, and salts thereof.

5. A pharmaceutical formulation comprising a compound according to claim 1 or a pharmaceutically-acceptable salt or ester thereof together with a pharmaceutically-acceptable carrier or diluent thereof.

6. A method for treating a disorder of the central nervous system which comprises administering an effective amount of a compound according to claim 1, or a pharmaceutically-acceptable salt thereof.

* * * * *